(12) United States Patent
Lovett et al.

(10) Patent No.: US 8,192,376 B2
(45) Date of Patent: Jun. 5, 2012

(54) SLEEP STATE CLASSIFICATION

(75) Inventors: Eric G. Lovett, Roseville, MN (US);
Robert J. Sweeney, Woodbury, MN (US); Bruce H. Kenknight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1734 days.

(21) Appl. No.: 10/643,006

(22) Filed: Aug. 18, 2003

(65) Prior Publication Data

US 2005/0043652 A1 Feb. 24, 2005

(51) Int. Cl.
| | |
|---|---|
| A61B 5/103 | (2006.01) |
| A61B 5/117 | (2006.01) |
| A61B 5/04 | (2006.01) |
| A61N 1/00 | (2006.01) |

(52) U.S. Cl. ............ 600/595; 600/587; 600/546; 607/9; 607/17

(58) Field of Classification Search .......... 600/546, 600/586, 595, 587
See application file for complete search history.

(56) References Cited

U.S. PATENT DOCUMENTS

| | | | |
|---|---|---|---|
| 4,836,219 A * | 6/1989 | Hobson et al. ............... | 600/595 |
| 4,846,195 A | 7/1989 | Alt | |
| 5,187,657 A | 2/1993 | Forbes | |
| 5,280,791 A * | 1/1994 | Lavie ............................ | 600/509 |
| 5,299,118 A * | 3/1994 | Martens et al. ............... | 600/509 |
| 5,466,245 A | 11/1995 | Heemels et al. | |
| 5,593,431 A | 1/1997 | Sheldon | |
| 5,645,570 A | 7/1997 | Corbucci | |
| 5,902,250 A * | 5/1999 | Verrier et al. ................ | 600/515 |
| 6,044,297 A | 3/2000 | Sheldon et al. | |
| 6,076,015 A | 6/2000 | Hartley et al. | |
| 6,270,457 B1 | 8/2001 | Bardy | |
| 6,312,378 B1 | 11/2001 | Bardy | |
| 6,331,536 B1 | 12/2001 | Radulovacki et al. | |
| 6,336,903 B1 | 1/2002 | Bardy | |
| 6,387,907 B1 * | 5/2002 | Hendricks et al. ........ | 514/254.06 |
| 6,398,728 B1 | 6/2002 | Bardy | |
| 6,514,218 B2 | 2/2003 | Yamamoto | |
| 6,517,497 B2 | 2/2003 | Rymut et al. | |
| 6,572,557 B2 * | 6/2003 | Tchou et al. ................. | 600/483 |

(Continued)

FOREIGN PATENT DOCUMENTS

EP 1 172 125 A1 1/2002

(Continued)

OTHER PUBLICATIONS

Richard L. Verrier et al., *Sleep, dreams, and sudden death: the case for sleep as an autonomic stress test for the heart*, Cardiovascular Research 31, pp. 181-211 (1996).

(Continued)

*Primary Examiner* — Max Hindenburg
*Assistant Examiner* — H. Q. Nguyen
(74) *Attorney, Agent, or Firm* — Hollingsworth & Funk, LLC

(57) ABSTRACT

Systems and methods for sleep state classification involve detecting conditions related to sleep, including at least one condition associated with rapid eye movement (REM) sleep. Additionally, a condition modulated by the sleep-wake status of the patient may be detected. A medical system that is partially or fully implantable incorporates sensors and circuitry for detecting and processing the sleep-related signals. A sleep state processor classifies the patient's sleep state based on the sleep-related signals. Sleep state classification may be used in connection with the delivery of sleep state appropriate therapy, diagnostic testing, or patient monitoring.

36 Claims, 11 Drawing Sheets

U.S. PATENT DOCUMENTS

| | | | |
|---|---|---|---|
| 6,658,292 | B2 | 12/2003 | Kroll et al. |
| 6,708,063 | B2 | 3/2004 | Czygan et al. |
| 6,752,766 | B2 | 6/2004 | Kowallik et al. |
| 6,907,288 | B2 | 6/2005 | Daum |
| 6,951,539 | B2 | 10/2005 | Bardy |
| 7,092,755 | B2 * | 8/2006 | Florio ................................ 607/9 |
| 7,168,429 | B2 | 1/2007 | Matthew et al. |
| 7,206,635 | B2 | 4/2007 | Cho et al. |
| 7,258,670 | B2 | 8/2007 | Bardy |
| 7,400,928 | B2 | 7/2008 | Hatlestad |
| 2003/0055461 | A1 | 3/2003 | Girouard et al. |
| 2003/0083241 | A1 * | 5/2003 | Young ................................ 514/9 |
| 2003/0111079 | A1 * | 6/2003 | Matthews et al. ........ 128/204.18 |
| 2003/0163059 | A1 | 8/2003 | Poezevera et al. |
| 2004/0111040 | A1 * | 6/2004 | Ni et al. ......................... 600/534 |
| 2004/0249299 | A1 * | 12/2004 | Cobb ............................. 600/529 |
| 2005/0119711 | A1 * | 6/2005 | Cho et al. ......................... 607/42 |

FOREIGN PATENT DOCUMENTS

| | | |
|---|---|---|
| JP | 2002519161 | 7/2002 |
| WO | WO0240096 | 5/2002 |
| WO | WO02087433 | 11/2002 |
| WO | WO03063954 | 8/2003 |
| WO | WO2004062485 | 7/2004 |
| WO | WO2005028029 | 3/2005 |

OTHER PUBLICATIONS

Olusola Ajilore, et al., *Nightcap: Laboratory and home-based evaluation of a portable sleep monitor*, Psychophysiology, 32, pp. 32-98 (1995).

Rihcard L. Verrier et al., *Sleep Related Cardiovascular Risk: New Home-Based Monitoring Technology for Improved Diagnosis and Therapy*, A.N.E., vol. 2, No. 2, pp. 158-175 (Apr. 1997).

Jan. 25, 2011, File History for U.S. Appl. No. 10/920,675.

Jan. 25, 2011, File History for U.S. Appl. No. 10/309,771.

Office action dated Feb. 22, 2006 from European application No. 03790304.4, 3 pages.

Office action response dated Sep. 4, 2006 from European application No. 03790304.4, 9 pages.

Office action dated Aug. 6, 2007 from European application No. 03790304.4, 6 pages.

Office action response dated Apr. 27, 2010 from European application No. 03790294.7, 8 pages.

International Search Report and Written Opinion dated Jul. 19, 2010 from European Application No. 08006191.4, 6 pages.

International Search Report and Written Opinion dated Jul. 26, 2010 from European Application No. 08075738.8, 4 pages.

Japanese Office Action dated Aug. 2, 2010 from Japanese patent application No. 2004557545, 2 pages.

Japanese Office Action dated Dec. 13, 2010 from Japanese patent application No. 2006-524027, 4 pages.

File History for U.S. Appl. No. 11/717,561 as retrieved from USPTO PAIR system on Nov. 10, 2011, 147 pages.

Appeal Decision for U.S. Appl. No. 10/920,675, as retrieved from USPTO PAIR system on Feb. 14, 2012, 13 pages.

Office Action Response for U.S. Appl. No. 11/717,561, filed Jan. 12, 2012 as retrieved from USPTO PAIR system on Feb. 14, 2012, 8 pages.

* cited by examiner

US 8,192,376 B2

SLEEP STATE CLASSIFICATION

FIELD OF THE INVENTION

The present invention relates generally to classification of sleep states.

BACKGROUND OF THE INVENTION

Sleep is generally beneficial and restorative to a patient, exerting great influence on the quality of life. As a person falls asleep, brain activity declines and there is a progressive increase in the depth of sleep. A typical night's sleep for a normal person quickly transitions to a sleep stage known as slow wave sleep (SWS) characterized by low frequency electroencephalogram (EEG) activity. At approximately ninety minute intervals, sleep lightens and a sleep state known as rapid eye movement (REM) sleep is initiated. REM sleep is characterized by high frequency EEG activity, bursts of rapid eye movements, skeletal muscle atonia, and heightened autonomic activity.

There are typically 4-6 REM periods per night, with increasing duration and intensity toward morning. While dreams can occur during either REM or SWS sleep, the nature of the dreams varies depending on the type of sleep. REM sleep dreams tend to be more vivid and emotionally intense than SWS sleep dreams. Furthermore, autonomic nervous system activity is dramatically altered when REM sleep is initiated.

In patients with respiratory or heart disease, the brain during sleep can precipitate breathing disturbances, myocardial ischemia, or arrhythmia. Although REM sleep is a necessary component of normal sleep, serious consequences may be associated with both the increase in autonomic activity and the intense emotional responses that accompany dreaming in patients with cardiovascular or respiratory disease. Knowledge of the patient's sleep state may be used to enhance diagnosis and/or treatment of various disorders.

SUMMARY OF THE INVENTION

The present invention is directed to classifying various sleep states. In one embodiment of the invention, a method involves sensing sleep-related conditions and using the detected sleep-related signals to classify one or more sleep states of a patient. The sleep-related conditions include at least one REM-modulated condition and at least one condition associated with a sleep-wake status of the patient. Classifying the one or more sleep states is performed at least in part implantably.

Another embodiment of the invention involves sensing a REM-modulated condition and using the REM-modulated condition to classify one or more sleep states. Classifying the one or more sleep states is performed at least in part implantably.

In a further embodiment of the invention, a medical system includes a detector system, having a sensor configured to sense a condition associated with REM sleep. The medical system further includes a classification system coupled to the sensor system and configured to classify one or more sleep states based on the condition associated with REM sleep. The classification system includes an implantable component.

In yet another embodiment of the invention, a medical system involves means for detecting conditions related to sleep, including a condition associated with a sleep-wake status of a patient and a condition associated with REM sleep. The system further includes means for classifying one or more sleep states based on the detected conditions. The means for classifying includes an implantable component.

In a further embodiment, a medical system includes means for sensing a condition associated with REM sleep and means for classifying a one or more sleep states based on the detected condition associated with REM sleep. The means for classifying the one or more sleep states includes an implantable component.

The above summary of the invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
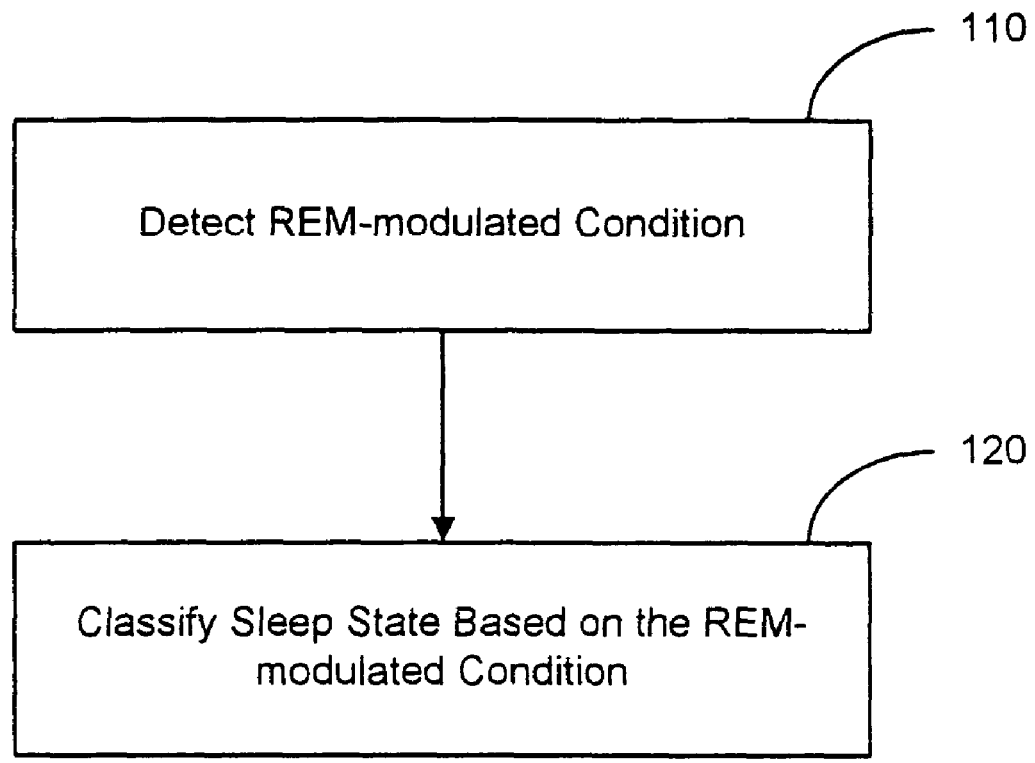
FIG. 1A is a flow graph of a method of sleep state classification in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

Sleep and its various states have been linked to an increase in respiratory and cardiac disorders, particularly for patients with cardiopulmonary disorders. For example, some epidemiologic studies note a peak incidence of sudden cardiac death around 5 to 6 am. One explanation for this peak suggests an association between the incidence of sudden death and episodes of rapid eye movement (REM) sleep, morning wakening or arousal. The mechanism eliciting fatal arrhythmia may be related to the intense phasic sympathetic modulation of the cardiovascular system during the REM state or morning wakening.

Non-REM sleep may also be linked to an increased likelihood of cardiac arrhythmia. Some patients are predisposed to nocturnal cardiac paroxysms associated with surges in vagal activity. Because non-REM sleep is associated with conditions of "vagal dominance," characterized by lower heart rate and low-to-high frequency power ratios, non-REM sleep may be implicated in these nocturnal arrhythmias.

Sleep may also be associated with increased respiratory disruptions. A significant percentage of patients between the ages of 30 and 60 experience some symptoms of disordered breathing, generally occurring during sleep. Sleep apnea is a particularly serious form of sleep-disordered breathing in which the patient may cease to breathe for periods of time. Obstructive apnea occurs when the patient's airway is obstructed by the collapse of soft tissue into the respiratory passage. Central sleep apnea is caused by a derangement of the central nervous system control of respiration. Patients suffering from central sleep apnea cease to breathe when control signals from the brain to the respiratory muscles are absent or interrupted.

Regardless of the type of sleep apnea, people experiencing an apnea event stop breathing for a period of time. The cessation of breathing may occur repeatedly during sleep, sometimes hundreds of times a night and sometimes for a minute or longer. Disordered breathing is associated with excessive daytime sleepiness, systemic hypertension, increased risk of stroke, angina and myocardial infarction. Respiratory disruption caused by sleep apnea and other disordered breathing episodes can be particularly serious for patients concurrently suffering from cardiovascular deficiencies, such as congestive heart failure.

Variations in disease, medication, etiology, and phenotype may all contribute to a patient's sleep state propensities to cardiac or respiratory disorders. Sleep state classification may be used to provide more effective therapy, better diagnostic information, and improved prognostic and preventive therapy capabilities. Sleep state classification in concert with therapy may result in improved therapy management for both cardiac and respiratory conditions, such as those described above. Tracking physiological changes during sleep states may also provide a mechanism for improved diagnosis of sleep-related disorders.

Diagnostic testing or therapeutic device testing may be advantageously performed during sleep or during particular sleep states. Diagnostic testing may involve, for example, assessing the patient's autonomic integrity during sleep and the possible use of REM episodes as a surrogate for stress testing. Performing diagnostic procedures during sleep recognizes opportunities afforded by sleep or particular sleep states to routinely perturb the cardiovascular system under controlled conditions to assess the patient's autonomic response.

Therapeutic device testing, such as AVI search, capture threshold, and cardiac template acquisition, may also be performed during sleep. Sleep provides a period of time to perform such therapeutic device tests while the patient's activity is low, resulting in more effective and consistent testing conditions.

Various embodiments of the invention involve sensing a physiological condition associated with REM sleep and using the REM condition to classify the patient's sleep states. REM-modulated conditions represent a group of physiological conditions that change during REM sleep and may be used to discern REM sleep from non-REM periods. REM sleep, as indicated by its name, is characterized by rapid bursts of eye movements, intense brain activity, and a general state of atonia, or skeletal muscle paralysis.

Various embodiments of the invention exploit the marked loss of skeletal muscle tone during REM to produce a REM-modulated signal. In this implementation, sensing a REM-modulated signal involves sensing the patient's skeletal muscle tone. Other REM-modulated signals may be used to detect REM sleep, including, for example, eye movement and brain wave activity. A representative set of sensors that may be used to sense REM-modulated signals include, for example, electroencephalogram (EEG) electrodes for detecting brain activity, electrooculogram (EOG) sensors for detecting eye movement, sensors for detecting muscle atonia, including electromyogram (EMG) sensors, strain gauge sensors, piezoelectric sensors, mechanical force sensor, or other transducers.

Sensing a condition associated with REM sleep may be used to discern REM sleep periods from non-REM periods. Sleep state classification may be further enhanced by detecting a condition associated with a sleep-wake status of the patient, the condition associated with the sleep-wake status indicating whether the patient is asleep or awake.

According to embodiments of the invention, a sleep state classification approach involves sensing sleep-related conditions, including at least one condition modulated by the sleep-wake status of the patient and a REM-modulated condition. The condition modulated by the sleep-wake status of the patient represents a condition that may be used to discriminate between periods of sleep and periods of wakefulness or arousal. Discriminating between periods of sleep and periods of wakefulness may be accomplished, for example, by sensing patient activity. According to this approach, if the patient's activity level is relatively low, e.g., below a sleep threshold, then the patient is determined to be asleep. The level of patient activity may be detected using an accelerometer, heart rate sensor, respiratory minute ventilation (MV) sensor or other types of sensors, for example.

Information derived from the REM-modulated condition may be used in combination with information related to the patient's sleep-wake status. This technique may be used to determine, for example, sleep onset and sleep offset, the duration and degree of arousals from sleep, and to classify sleep states including REM and non-REM states.

In accordance with embodiments of the invention, a sleep state classification processor receives the outputs of the one or more sensors configured to sense signals associated with the sleep-related conditions. The sleep state processor may perform sleep state classification on a real-time basis, or may process previously acquired and stored sensor data in a batch mode to retrospectively classify the sleep states of one or more sleep periods.

Sleep state classification may involve an adaptive approach, wherein the sleep state processor learns the physiological responses of a patient in various sleep states. The learned responses may be used to enhance the accuracy and/or sensitivity of the sleep state classification. Adaptive sleep state classification may involve monitoring the changes in one or more physiological signals over a period of time and adjusting thresholds used for determining sleep onset, sleep offset, and various sleep states to accommodate the drift or other changes in the sleep-related signals.

In one configuration, one or more of the sensors used to detect the sleep-related conditions, e.g., the REM-modulated condition and/or the condition associated with the patient's sleep-wake status, may be implantable, or may utilize an implantable component. In another configuration, the sleep state processor may be partially or fully implantable. In other configurations, both the sensors and the sleep state processor may be implantable or use implantable components.

As previously discussed, sleep state classification may be useful in coordinating sleep state informed therapy delivery to treat various disorders and to perform sleep state informed testing and monitoring. In one example implementation, cardiac therapy may be triggered during particular sleep states to reduce the likelihood of cardiac arrhythmia during vulnerable sleep periods. In a similar manner, sleep state classification may be used to trigger disordered breathing therapy to preclude or reduce episodes of sleep-disordered breathing.

The flow graph of FIG. 1A depicts a method of classifying sleep states according to embodiments of the invention. A REM-modulated condition e.g., brain activity, eye movement, and/or muscle atonia, is detected 110 and is used to classify 120 the patient's sleep state. Classifying the one or more sleep states is performed at least in part implantably. Using the detected REM-modulated condition, the system may determine that the patient is in a REM sleep state or in a non-REM period, for example.

Figure 1B:
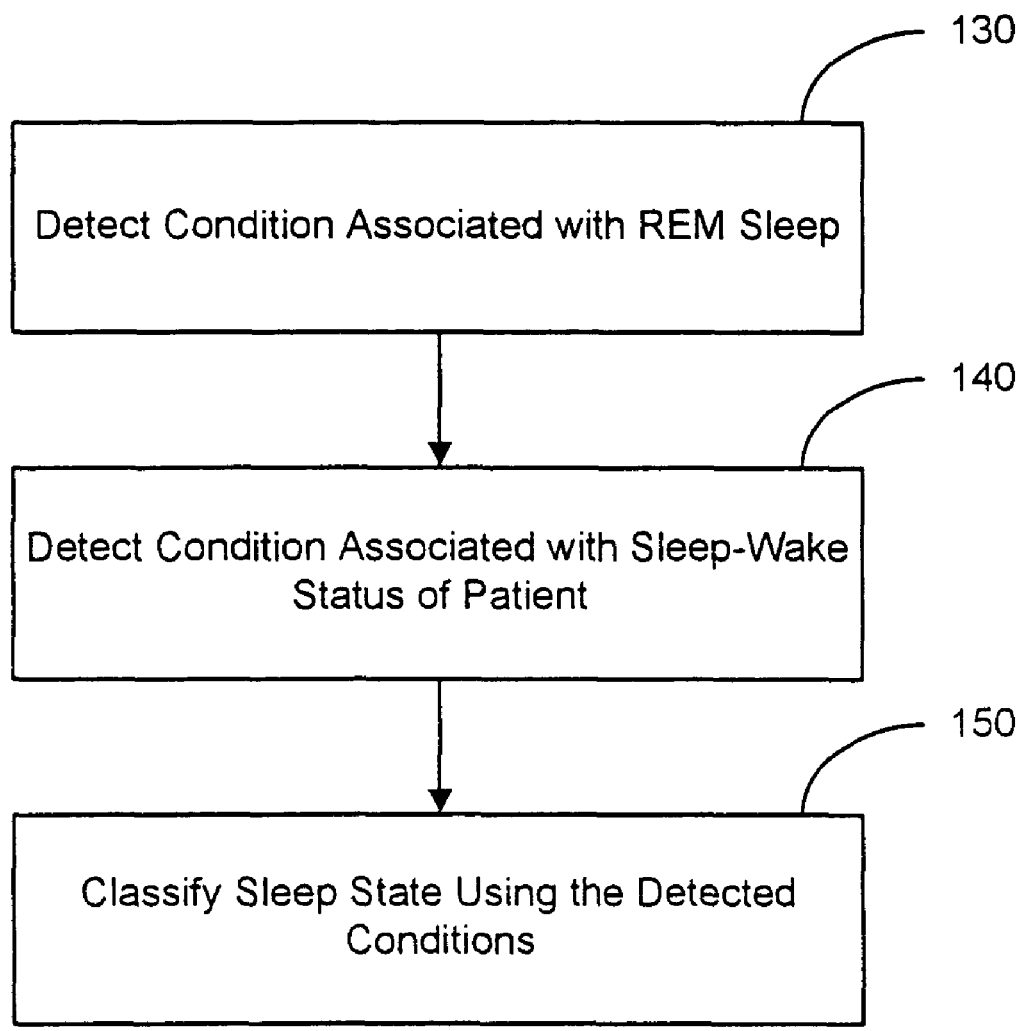
FIG. 1B is a flow graph of a method of sleep state classification involving at least one condition associated with REM sleep and at least one condition associated with a sleep-wake status of a patient in accordance with embodiments of the invention.

Another method for classification of sleep states in accordance with embodiments of the invention is illustrated in the flow graph of FIG. 1B. The method involves detecting sleep-related conditions including at least one REM-modulated condition 130 and at least one condition 140 associated with a sleep-wake status of the patient. Sleep state classification is performed 150 based on the detected conditions. Classifying the one or more sleep states is performed at least in part implantably.

Figure 2:
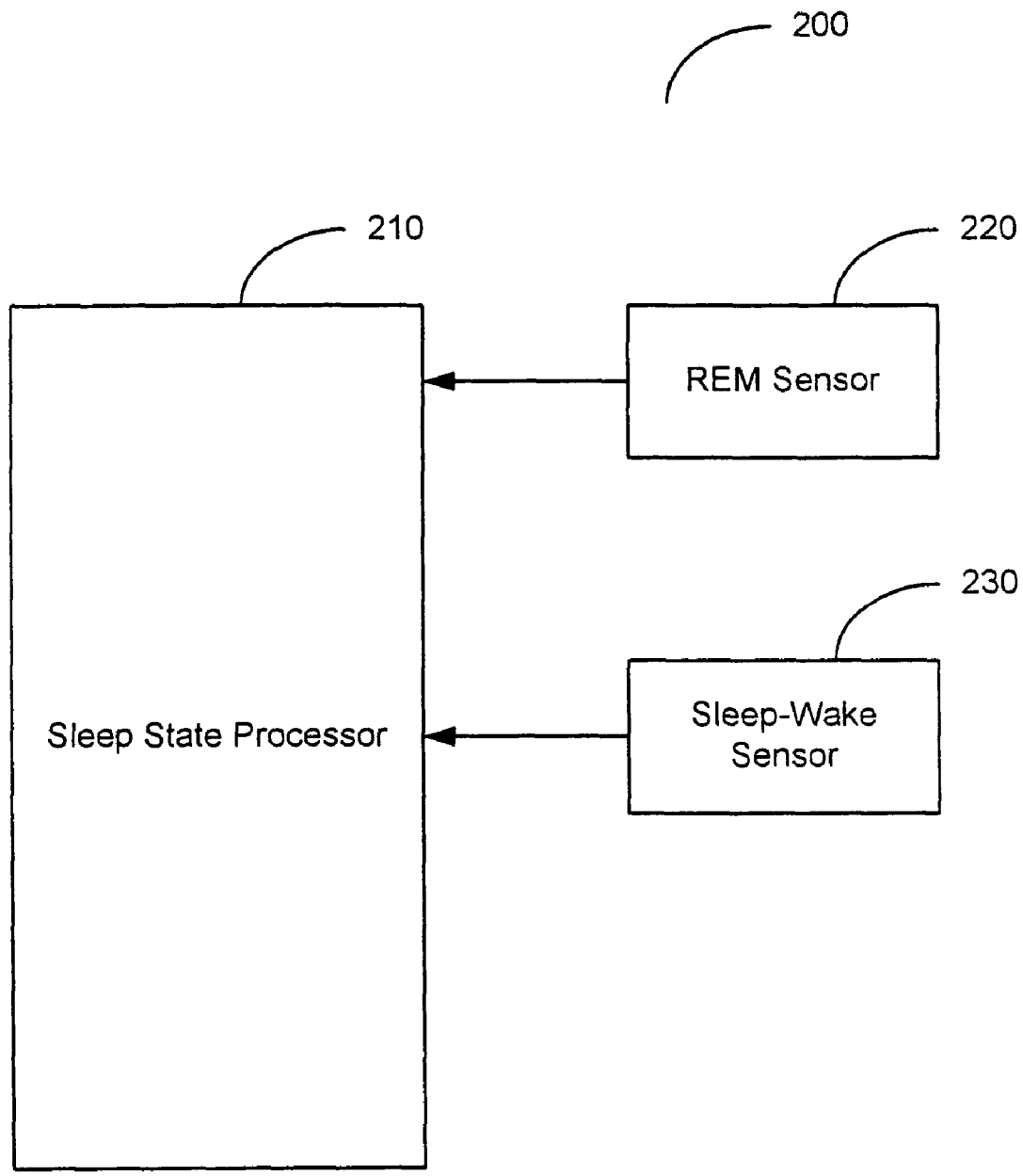
FIG. 2 is block diagram of system suitable for implementing a sleep state classification method in accordance with embodiments of the invention.

A block diagram of a system 200 suitable for implementing a sleep state classification method according to embodiments of the invention is illustrated in FIG. 2. The sleep state classification system 200 may include one or more sensors 230 used to sense a physiological signal associated with the sleep-wake status of the patient. In one example implementation, the sleep-wake sensor 230 may be responsive to patient activity. When the patient's activity falls below a threshold, the patient is considered to be asleep. When the patient's activity rises above the activity threshold, the patient is considered to be awake. Other methods of detecting whether the patient is asleep or awake are also possible.

The system further includes a REM sensor 220 sensitive to a REM-modulated physiological condition. REM sleep detection may be implemented by comparing the output of a skeletal muscle tone sensor to a threshold, for example. When the REM sensor output indicates loss of muscle tone consistent with a REM sleep threshold, the patient is determined to be in REM sleep. The sleep-wake sensor 230 and the REM sensor 220 may optionally be used in cooperation with additional sensors employed to detect additional sleep-related conditions. The additional sleep-related conditions may be used to augment the accuracy, sensitivity, or other functional capabilities, of the sleep state classification system 200. For example, a patient posture or torso orientation sensor may be used in combination with a patient activity sensor to provide enhanced detection of the sleep-wake status of the patient. If the patient's activity is low, as indicated by the output of a patient activity sensor, and the patient is lying down, as indicated by the output of a torso orientation sensor, then the combination of the two conditions may allow for more accurate sleep onset detection.

The REM sensor 220, the sleep-wake status sensor 230, and any additional sensors are coupled to a sleep state processor 210 that detects and processes the sensor outputs. The sleep state processor 210 may use outputs from the sleep-wake sensor 230 and the REM sensor 220 to determine if the patient is awake or asleep, to determine the duration and degree of arousals from sleep, to classify sleep states including REM and non-REM states, and to determine the duration of various sleep states, for example.

In one embodiment, one or both the REM sensor 220 and the sleep-wake sensor 230 are positioned external to the patient and the sleep state processor 210 is implantable or includes an implantable component. In another embodiment, one or both the REM sensor 220 and the sleep-wake sensor 230 are fully or partially implantable and the sleep state processor 210 is positioned externally to the patient. In yet another embodiment, the REM sensor 220, sleep-wake sensor 230, and the sleep state processor 210 all include implantable components or are fully implantable.

Components of the sleep state classification system 200 may employ wireless communications. For examples, the REM sensor 220 and sleep-wake sensor 230 may be coupled to the sleep state processor 210 using a wireless communications link. In one example, some or all of the sensors 220, 230 use remote communication capabilities, such as a wireless proprietary or a wireless Bluetooth communications link.

The sleep state processor 210 may adaptively classify sleep states by learning patient responses in connection with various sleep states. In one example, the sleep state processor 210 may perform sleep state classification by comparing sensor signal levels to predetermined thresholds. Initial thresholds may be established using clinical data derived from a group of individuals, or using patient-specific data. After initial thresholds have been established, the sleep state processor 210 may update the thresholds to provide more sensitive and/or more accurate sleep state classification based on data acquired from the patient over time. A sleep state threshold may be updated by a recent history of the sensor output level associated with a particular sleep state. This process may involve collecting data over time to determine the sleep patterns of the patient and adjusting the thresholds based on the sleep patterns. By this process, initially established thresholds, e.g., sleep onset threshold for an accelerometer output, or REM sleep threshold for an EMG sensor output, may be modified as additional data is acquired from the patient regarding the relationship between the sensor output levels and patient's sleep state.

Figure 3:
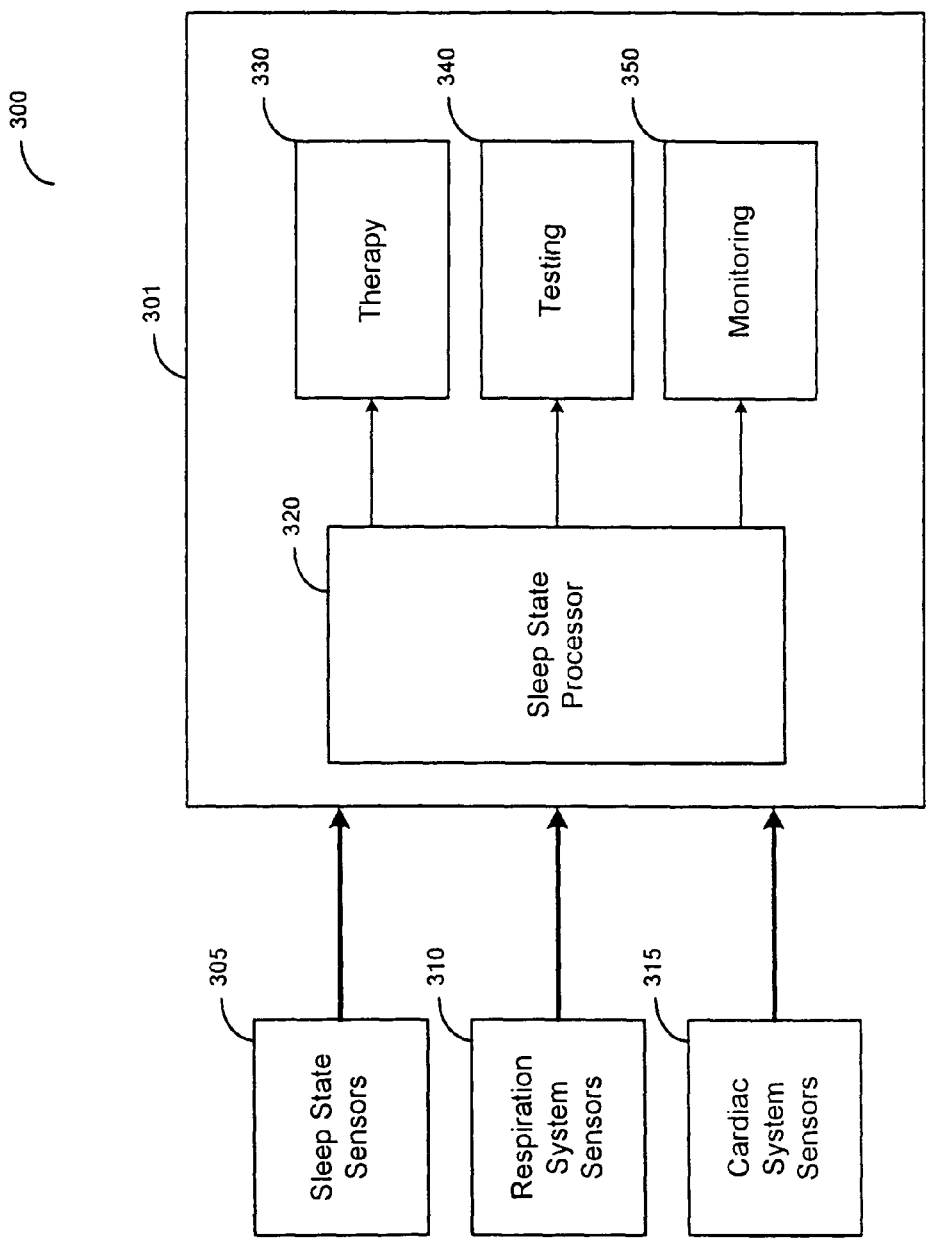
FIG. 3 is a block diagram of a medical device utilizing a sleep state classification system implemented in accordance with embodiments of the invention.

FIG. 3 presents a block diagram illustrating a medical system 300 utilizing a sleep state classification system implemented in accordance with embodiments of the invention. Such a medical system 300 may be employed, for example, to perform sleep state informed diagnostic monitoring and/or diagnostic testing to assess the capabilities of the patient's physiological systems. Such diagnostic monitoring or testing may involve one or more physiological systems, including, for example, the cardiac and respiratory systems. Additionally, or alternatively, the medical system 300 may be used to provide sleep state informed therapy to a patient, for example, cardiac rhythm therapy, respiratory therapy, or other types of therapy enhanced by sleep state classification. Further, the medical system 300 may be used to perform sleep state informed therapeutic device testing. Such a medical system 300 may be purely or predominantly diagnostic in function, purely or predominantly therapeutic in function, or may perform a combination of therapeutic and diagnostic operations.

The medical system 300 includes a medical device 301 coupled to a variety of sensors 305, 310, 315. The sensors 305, 310, 315 provide physiological information used in connection with sleep state classification and the therapeutic and/or diagnostic operations performed by the medical device 301. The sleep state sensors 305 include a sensor capable of detecting a REM-modulated condition, such as skeletal muscle atonia. Additional sleep state sensors, including one or more sensors indicative of the sleep-wake status of the patient, e.g., a patient activity sensor, may also be used.

The medical device 301 may also be coupled to sensors 310, 315 configured to detect one or more aspects of the patient's physiological systems, including, for example, the cardiac and/or respiratory functions of a patient. In various configurations, the medical system 300 may monitor, test, or provide therapy to the patient, including cardiac and/or respiratory therapy. In one implementation, cardiac sensors 315, e.g., cardiac electrodes, may be used to sense the electrical activity of the heart. The cardiac system sensors may comprise patient-internal or patient-external cardiac electrodes electrically coupled to the patient's heart tissue, for example.

The medical device 301 may be coupled to one or more respiratory system sensors 310 capable of detecting conditions associated with the respiratory functions of the patient. In one embodiment, the respiratory functions of the patient may be monitored using a transthoracic impedance sensor. Transthoracic impedance tracks the patient's respiratory effort, increasing upon respiratory inspiration and decreasing upon respiratory expiration. The transthoracic impedance signal may be used to determine the patient's respiration tidal volume (TV), minute ventilation (MV), and/or other respiratory parameters, for example. Sensors other than, or in addition to, the cardiac and respiration system sensors described herein may be used to detect cardiac and/or respiration functions of the patient.

The sleep state processor 320 uses information from the sleep state sensors 305 to determine the states of the patient's sleep, including, for example, sleep onset, termination, REM and non-REM states. Information generated by the sleep state processor 320 may be used by other components of the medical device 301 to provide therapy, testing, and/or monitoring coordinated with the patient's sleep state.

Sleep state information may be provided to a therapy module 330 coupled to the sleep state processor 320. The therapy module 330 controls the delivery of sleep state informed therapy to the patient. For example, cardiac therapy may be coordinated using sleep state classification information to provide cardiac arrhythmia therapy during REM or other proarrhythmic sleep periods. Sleep state classification may also be used, for example, in connection with delivery of sleep informed therapy to preclude or reduce episodes of disordered breathing while the patient is asleep. Other types of therapy may also be enhanced using sleep state classification.

The sleep state processor 320 may be coupled to a monitoring unit 350 configured to collect and store historical data acquired from the sleep state sensors 305, respiratory system sensors 310, the cardiac system sensors 315, and/or other components of the medical device 301. The monitoring unit 350 may track one or more patient conditions and provide data used in the analysis of various physiological processes. The monitoring module 350 may collect data useful in assessing trends of various physiological systems. Trending data may be used in combination with sleep state classification to identify gradual changes in the patient's physiological conditions, especially those altered by sleep, or by particular sleep states.

A testing module 340 may be implemented within the medical device 301 to control diagnostic tests and/or to control device testing to maintain or improve the operation of the medical device 301. Information from the sleep state processor 320 is used by the testing module 340 to ensure that diagnostic and/or device testing appropriately coincides with a sleep or waking state of the patient, or to a particular state of sleep.

Diagnostic testing may be employed to investigate the functioning of one or more of the patient's physiological systems. Diagnostic testing may include changing one or more parameters of the patient's therapy, e.g., cardiac rhythm therapy, and assessing the impact of the change on the patient. For example, the patient's therapy regime may be altered during sleep, or during a particular sleep state, to determine the effect of the change on the patient.

In one implementation, diagnostic testing may be performed within the structure of an advanced patient management system. Advanced patient management systems allow physicians to remotely and automatically monitor patient conditions and test physiological functions, including cardiac and respiratory functions, for example. In one example of advanced patient management, an implantable cardiac rhythm management system, such as cardiac pacemaker, defibrillator, or resynchronization device, may be equipped with various telecommunications and information technologies enabling real-time data collection, diagnosis, and treatment of the patient. Diagnostic testing performed by advanced patient management devices may be enhanced by the ability to perform testing in a sleep coordinated setting. Systems and methods involving advanced patient management techniques are described in U.S. Pat. Nos. 6,336,903, 6,312,378, 6,270,457, and 6,398,728 which are incorporated herein by reference in their respective entireties.

A diagnostic testing methodology may use sleep state classification to determine the general behavior of the patient's physiological responses in connection with various sleep states. Such a process may involve determining the patient's intrinsic responses to normal variations in physiologic processes. In addition, the patient's evoked physiological responses to device-based stimuli may also be determined.

In one implementation of sleep coordinated diagnostic testing, non-REM sleep may present an opportunity to perform automatic or physician activated diagnostic testing under relatively controlled circumstances. The medical device 301 may perform diagnostic testing during non-REM sleep when the patient's activity is low. In one configuration, the medical device 301 may modify or implement a particular cardiac pacing regimen during a non-REM period to determine the effect of such modification on the patient's cardiac system.

In addition to diagnostic testing, various device testing procedures may preferably be conducted while the patient's activity is low, such as during non-REM sleep. For example, a medical device 301 providing cardiac rhythm management therapy may perform device testing to improve or modify a pacing regimen during the non-REM sleep state. In one implementation, a pacemaker may perform tests during non-REM sleep to optimize a pacing escape interval, such as the AV delay of a dual chamber or bi-ventricular device. In another example, a pacemaker may adjust pacing energy levels based on a capture threshold test performed during non-REM sleep. In yet another embodiment, a cardiac rhythm management system may use non-REM sleep as an opportune period of low patient activity to acquire or update cardiac waveform morphological templates used to identify various cardiac arrhythmias.

Figure 4:
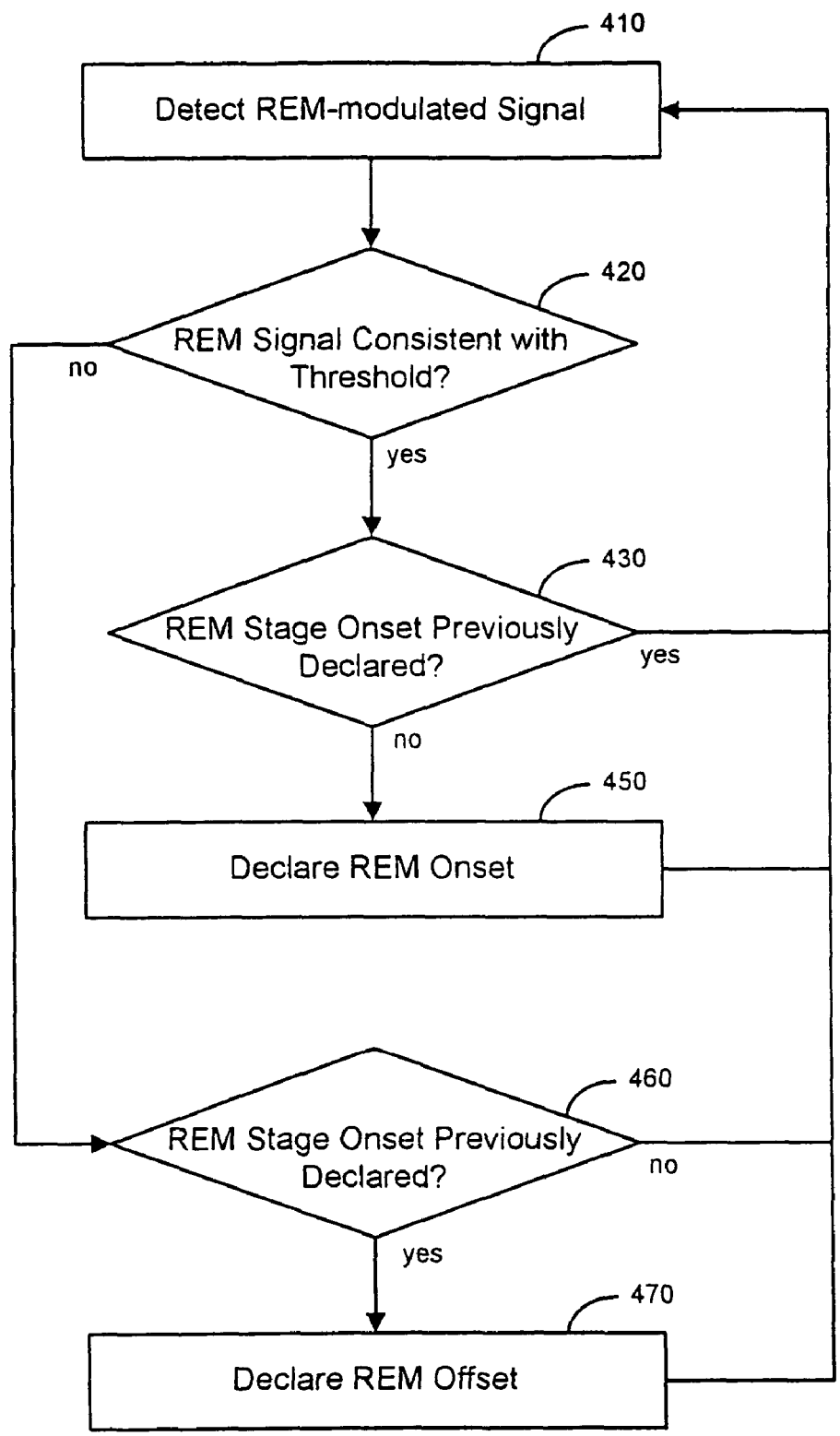
FIG. 4 is a flow graph illustrating a method of performing sleep state classification by determining a period of REM sleep in accordance with embodiments of the invention.

The flow graph of FIG. 4 illustrates a method of performing sleep state classification in accordance with embodiments of the invention. The method involves detecting 410 at least one REM-modulated signal, e.g., a signal modulated by muscle atonia. If the REM-modulated signal is consistent 420 with a predetermined REM sleep threshold, then the system determines if REM sleep onset has previously been declared 430. If REM sleep onset was not previously declared 430, then the system declares REM sleep onset 450.

If the REM-modulated signal is not consistent 420 with the predetermined REM sleep threshold and REM sleep onset was previously declared 460, then REM sleep offset is declared 470. If the REM-modulated signal is not consistent 420 with the REM sleep threshold and REM onset was not previously declared 460, the system continues to sense 410 the REM-modulated signal to detect REM sleep onset.

Figure 5:
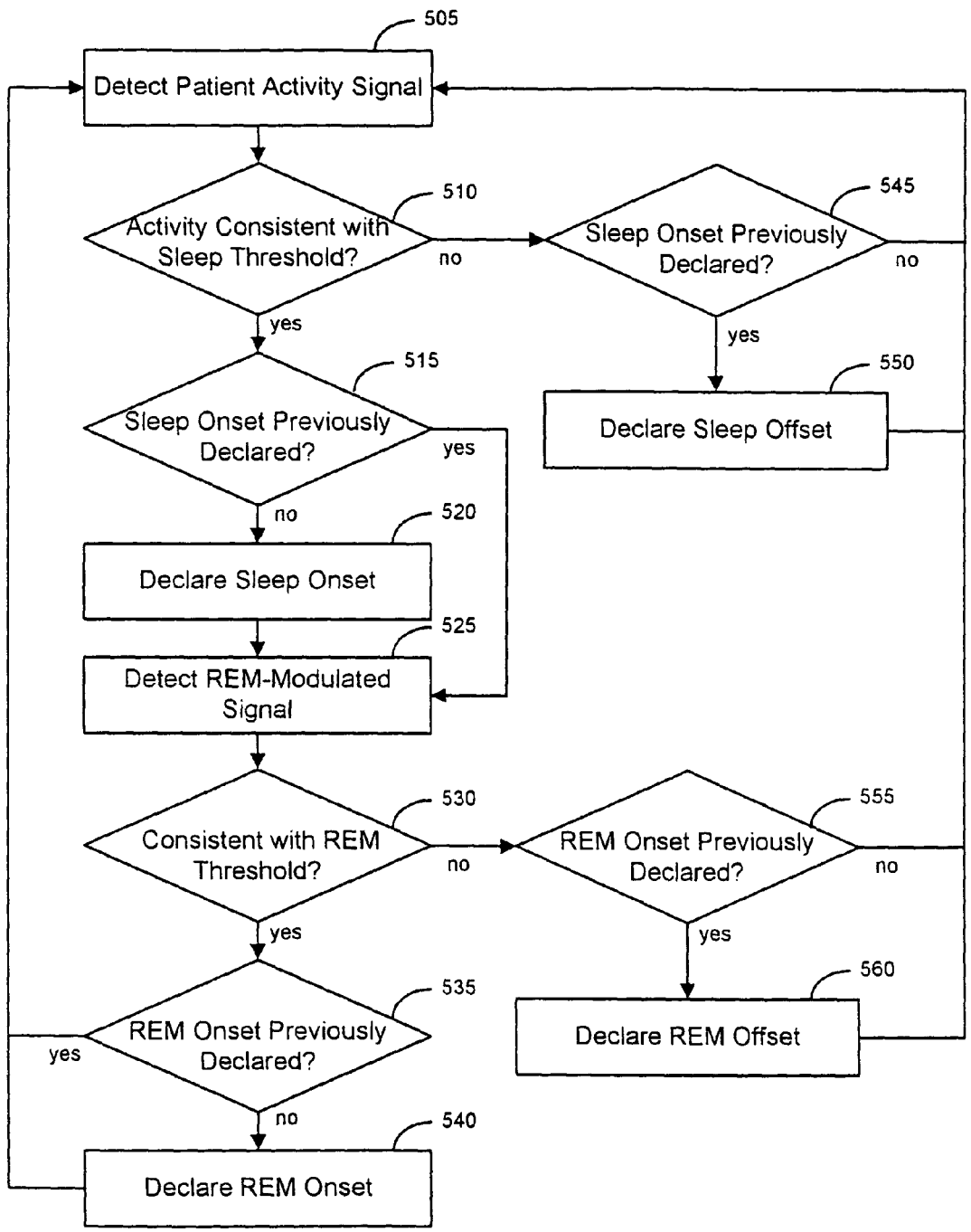
FIG. 5 is a flow graph of a method of using a patient activity signal in combination with a REM-modulated signal to classifying sleep states in accordance with embodiments of the invention.

The flow graph of FIG. 5 illustrates a method of using a sleep-wake condition in combination with a REM-modulated condition to classify sleep states according to embodiments of the invention. According to this implementation, the system determines sleep onset and sleep offset by comparing a patient activity signal to a threshold. Various methods of sleep onset and sleep offset detection may be used in connection with the sleep state classification approaches of the present invention. Methods and systems related to sleep detection are further described in commonly owned U.S. Pat. No. 7,189,204 (Ni et al.) and incorporated by reference herein in its entirety.

The method illustrated in FIG. 5 involves determining REM sleep onset and offset using a REM-modulated signal. REM sleep periods may be classified as intervals between REM onset and offset. Non-REM sleep periods may be classified as intervals between sleep onset and offset that are not classified as REM sleep.

A signal related to the activity level of the patient, e.g., accelerometer signal, is detected 505 and compared 510 to a predetermined sleep threshold. If the patient's activity level is consistent 510 with the sleep threshold, and if sleep onset was previously declared 515, the system detects 525 a REM-modulated signal. If the patient's activity level is consistent 510 with the sleep threshold and if sleep onset was not previously declared 515, the system declares sleep onset 520 and detects 525 the REM-modulated signal.

If the REM-modulated signal level is consistent 530 with a REM sleep threshold, and REM sleep onset 535 was not previously declared, then REM sleep onset is declared 540. If the REM-modulated signal level is not consistent 530 with the REM sleep threshold and REM onset was previously declared 555, then REM sleep offset is declared 560.

Figure 6:
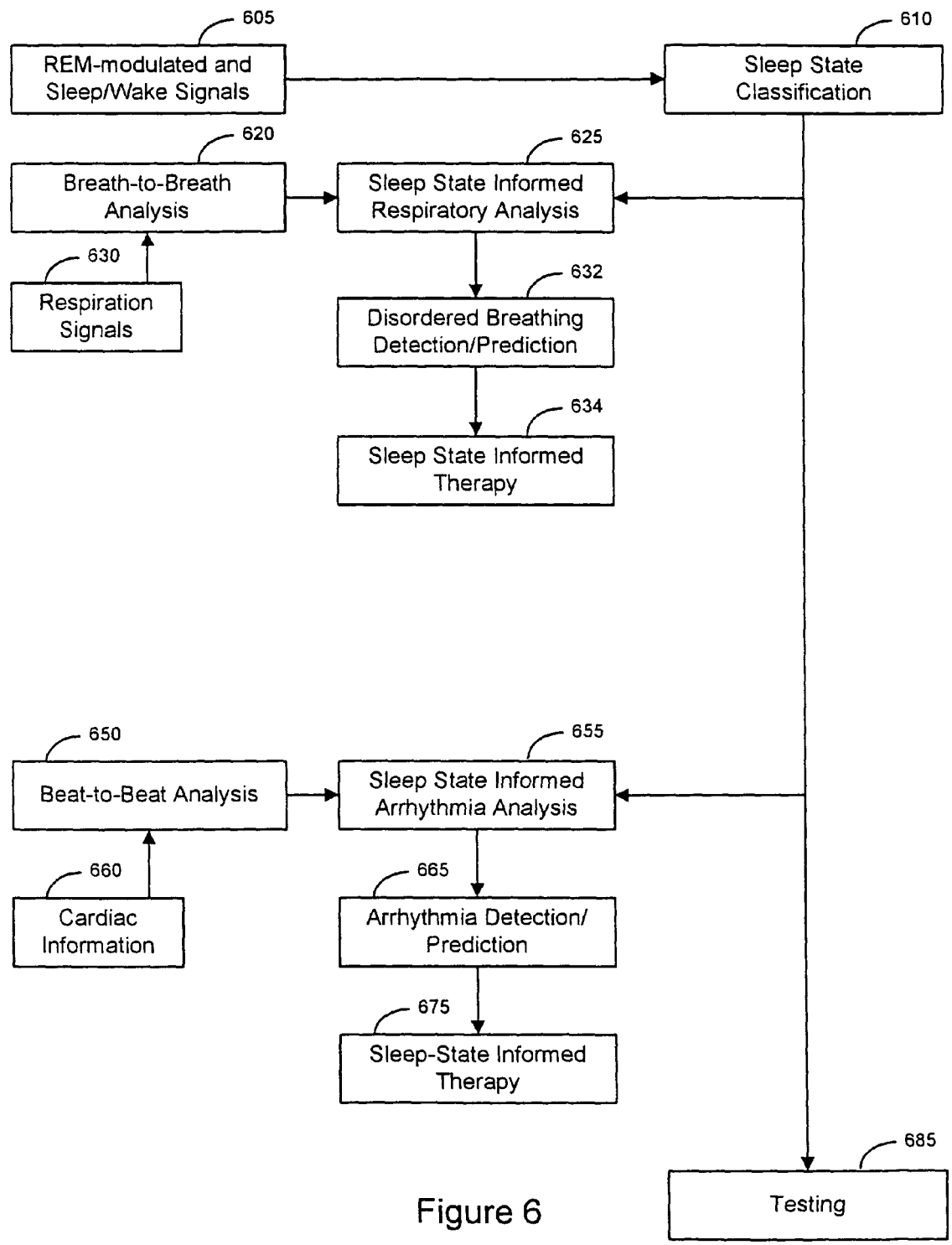
FIG. 6 is a process flow diagram illustrating sleep state determination in cooperation with therapy delivery and testing in accordance with embodiments of the invention.

Using the method illustrated in FIG. 5, sleep onset, offset, REM, and non-REM sleep may be detected. Periods of REM and/or non-REM sleep may be advantageously used in connection with a number of diagnostic and therapeutic operations, as previously discussed. FIG. 6 is a process flow diagram illustrating a process for using sleep state classification in cooperation with therapy delivery and testing in accordance with embodiments of the invention.

As presented in the process flow diagram of FIG. 6, the system detects 660 cardiac signals and analyzes 650 the cardiac signals on a beat-to-beat basis. Beat-to-beat cardiac signal analysis 650 may be used to perform arrhythmia detection 665 based on rate and/or morphological analysis techniques, for example. Depending on the type of arrhythmia detected, if any, an appropriate therapy 675 may be delivered to the heart.

In one implementation, bradycardia pacing therapy may be delivered to the heart to maintain the patient's rhythm at a hemodynamically sufficient rate. In other examples, a variety of tiered tachyarrhythmia therapies, including, for example, anti-tachycardia pacing, cardioversion, and/or defibrillation may be available to treat detected cardiac tachyarrhythmias.

The illustrative system utilizes REM-modulated and sleep/wake condition signals 605 for sleep state classification 610. Sleep state classification 610 may be used in cooperation with the beat-to-beat cardiac signal analysis 650 to implement sleep state informed arrhythmia analysis 655, thus augmenting the delivery of cardiac arrhythmia therapy 675. In one example, bradycardia pacing therapy may be enhanced by the ability to switch to a lower pacing rate when the patient is determined to be asleep. Such a procedure may be advantageous, for example, both to increase the device lifetime and to reduce stress on the heart. In a further example, preventive arrhythmia therapy 675 may be delivered during sleep or based on prediction of future arrhythmic events, e.g., upon detection of a pro-arrhythmic sleep state 665. In one example, preventive arrhythmia therapy may be delivered to prevent tachyarrhymias known to occur more frequently during REM sleep or during arousal from sleep.

Sleep state classification may also be used in connection with therapy to terminate or prevent sleep-disordered breathing. Various therapies may be implemented to treat sleep-disordered breathing, including maintaining continuous positive air pressure to prevent collapse of tissue into the respiratory passage, electrical stimulation of nerves or muscles, and cardiac pacing therapy, for example. Because disordered breathing is more likely to occur when the patient is asleep, disordered breathing detection or prediction 632 may be augmented by employing sleep state informed respiratory analysis 625 in accordance with embodiments of the present invention.

Detection of disordered breathing may be accomplished by detecting 630 respiration signals representing the patient's breathing cycles and analyzing each breath 620. In one implementation, disordered breathing, including, e.g., hypopnea and apnea, may be detected 632 by monitoring the respiratory waveform output produced by a transthoracic impedance sensor.

When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Another method of detecting 632 disordered breathing involves analyzing the patient's respiratory patterns. According to this method, the patient's respiratory cycle is divided into several periods, including, inspiration, expiration, and non-breathing periods. The inspiration, expiration, and non-breathing respiratory periods are analyzed for patterns consistent with various types of disordered breathing. Methods and systems for detecting disordered breathing based on respiration cycle patterns are more fully described in commonly owned U.S. Pat. No. 7,252,640 (Ni et al.) and incorporated herein by reference.

Methods and systems for predicting disordered breathing are described in commonly owned U.S. Pat. No. 7,396,333 (Stahmann et al.) and incorporated herein by reference. As described in the above-referenced patent application, sleep-disordered breathing may be predicted based on a number of patient conditions that increase the likelihood of disordered breathing. Conditions that predispose the patient to disordered breathing include, for example, air pollution, alcohol use, and pulmonary congestion, among other conditions. In addition to predisposing conditions that make disordered breathing more likely, various precursor conditions may be used to determine that a disordered breathing episode is imminent. For example, blood chemistry, hyperventilation, and the regular periodicity of previous disordered breathing episodes may be used to predict an imminent onset of disordered breathing.

If disordered breathing is detected or predicted 632, an appropriate therapy 634 may be provided to terminate or prevent the disordered breathing. Disordered breathing therapy 634 may include, for example, cardiac pacing, nerve stimulation, or other types of disordered breathing therapy, such as those previously discussed. Methods and systems for providing therapy to mitigate disordered breathing based on the prediction or detection of disordered breathing are described in commonly owned U.S. Pat. No. 7,680,537 (Stahmann et al.) and U.S. Pat. No. 7,720,541 (Stahmann et al.), respectively, both incorporated herein by reference in their respective entireties.

Sleep state classification 610 may also be used to identify preferable periods of time for performing 685 various testing procedures, including, for example, diagnostic testing and/or testing of therapeutic device parameters. In various implementations, sleep state informed diagnostic testing may allow testing to assess the patient's autonomic integrity. Sleep state classification may further allow the use of REM episodes as a surrogate for stress testing, and recognition of opportunities to routinely perturb the cardiovascular system under controlled conditions.

Sleep state classification also provides an opportunity to test one or more parameters of a therapeutic device while the patient's activity is low. Such testing may involve, for example, capture threshold testing for a cardiac pacing device and cardiac signal morphology template acquisition to be used in connection with cardiac arrhythmia detection. Thus, sleep state classification may be used to provide more effective therapy, better diagnostic information, and improved prognostic and predictive capabilities.

Figure 7:
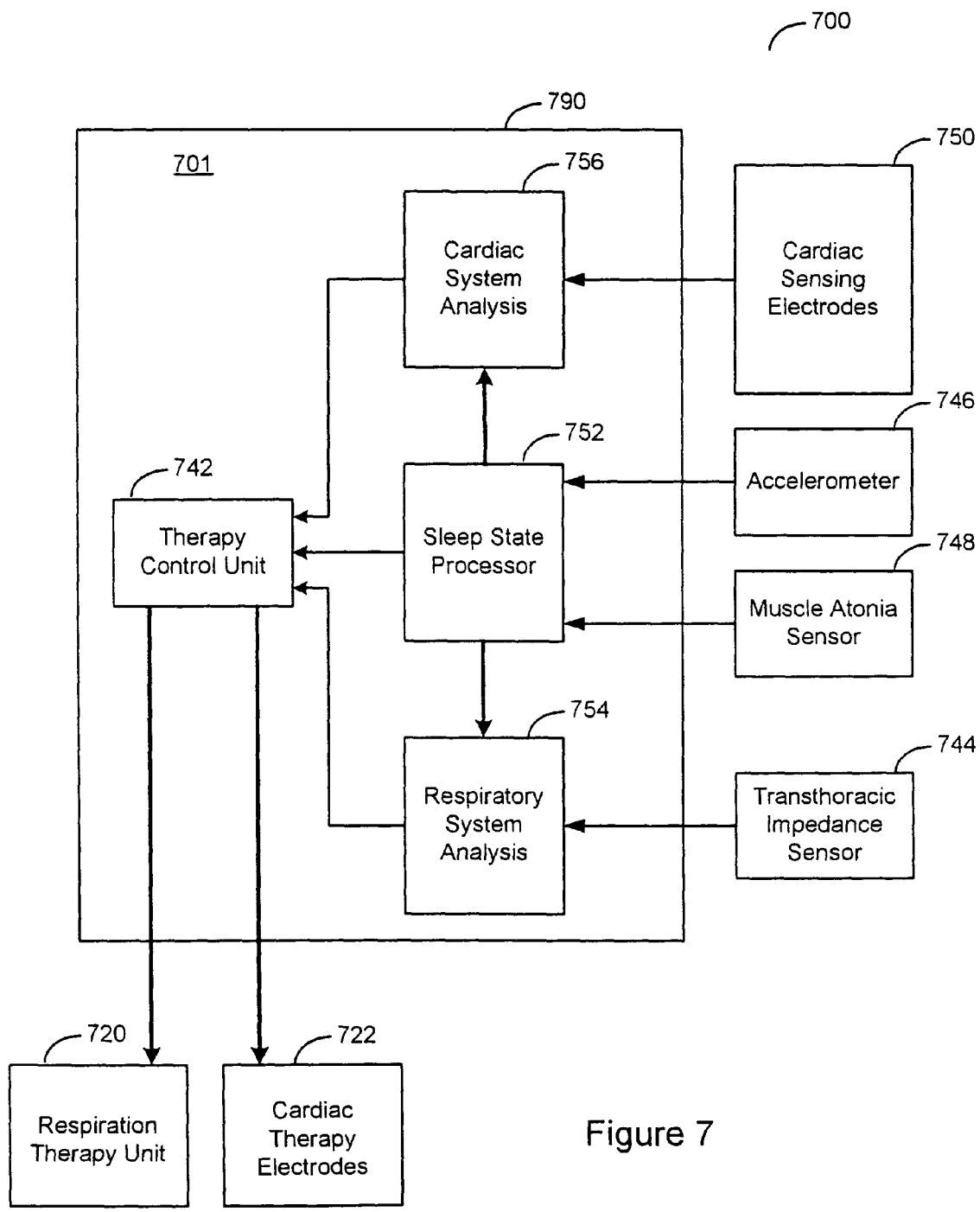
FIG. 7 is a block diagram of a medical device that may be used to perform sleep state informed therapy in accordance with embodiments of the invention.
Figure 8:
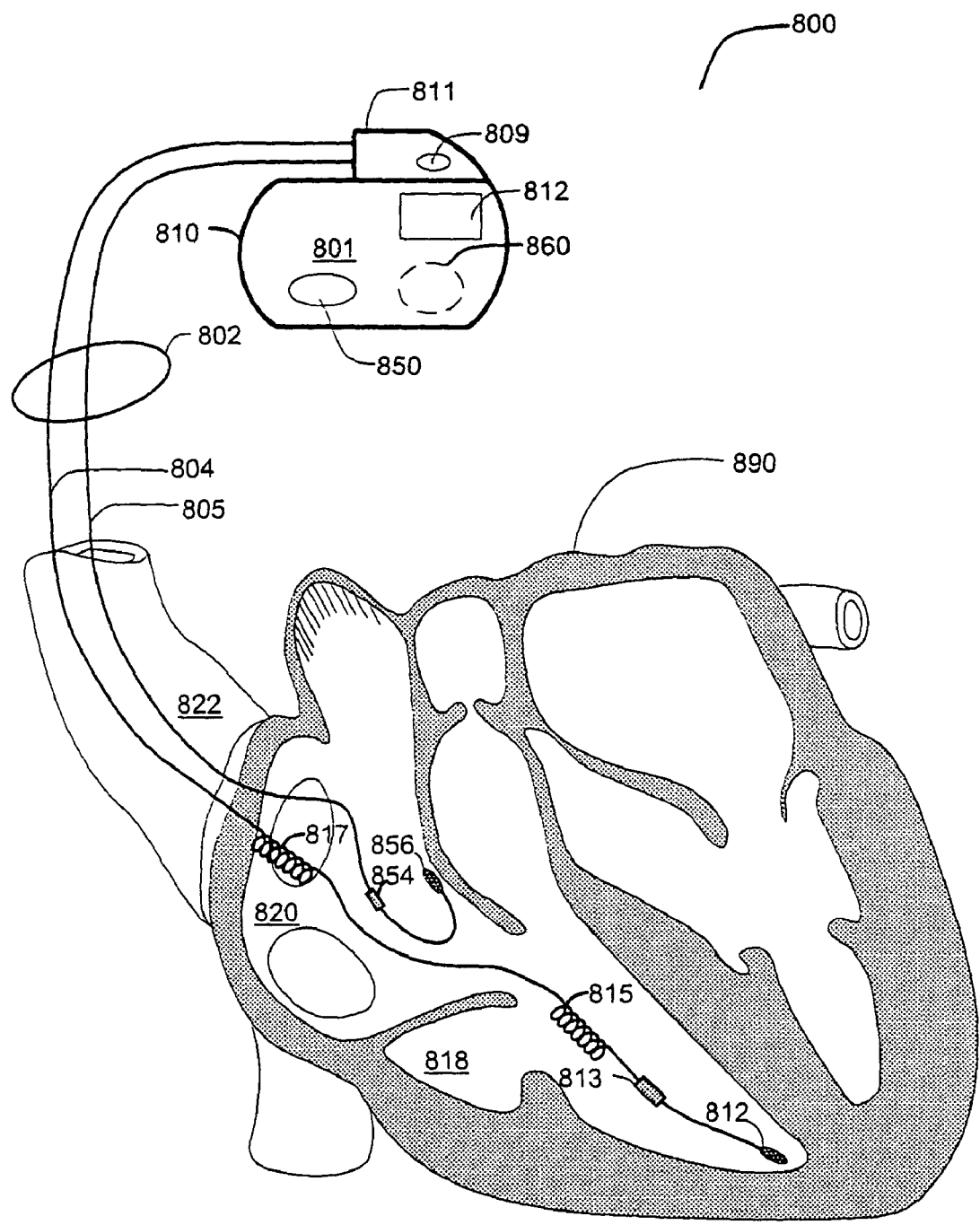
FIG. 8 is partial view of an implantable medical device that may used to perform sleep state informed therapy in accordance with embodiments of the invention.

FIGS. 7 and 8 illustrate a medical system that may be used to perform sleep state informed therapy in accordance with embodiments of the invention. The block diagram of FIG. 7 shows the medical system 700 divided into functional blocks. It will be appreciated by those skilled in the art that there exist many possible configurations in which these functional blocks can be arranged and implemented. The example depicted in FIG. 7 is one possible functional arrangement.

FIG. 7 illustrates an implantable cardiac pulse generator 701 enclosed in a housing 790 and configured to provide therapy for cardiac arrhythmia. Various cardiac rhythm therapies, including bradycardia pacing, anti-tachycardia pacing, defibrillation, and cardioversion, may be implemented in cooperation with sleep state classification in accordance with embodiments of the invention.

Optionally, the medical device 700 may also be configured to detect respiratory disorders, e.g., sleep-disordered breathing, and to provide therapy to mitigate the respiratory disorders. Disordered breathing therapy, including cardiac pacing and/or other types of disordered breathing therapy, such as continuous positive air pressure (CPAP), nerve stimulation, muscle stimulation or other therapy for treating disordered breathing, may be controlled or provided by components of the cardiac pulse generator 701.

Although FIG. 7 depicts a sleep state classification system implemented in a cardiac pulse generator 701, it is understood that configurations, features, and combinations of features described in the disclosure may be implemented in a number of medical devices. Sleep state classification may be implemented in connection with various diagnostic and therapeutic devices and such embodiments and features are not limited to the particular devices described herein.

Further, although various embodiments involve devices or systems having an implantable control system and implantable sensors, it is understood that therapy or diagnostic systems utilizing the sleep state classification methodologies of the present invention may be configured so that the control system or components of the control system are arranged externally to the patient. The sensors and the control system, and in particular the patient sleep state classification system, may involve patient-external components, patient-internal components or a combination of patient-external and patient-internal components.

In the embodiment illustrated in FIG. 7, the implantable pulse generator 701 includes circuitry for providing cardiac rhythm therapy 742 to treat various arrhythmic conditions. Cardiac arrhythmia therapy is implemented by detecting electrical signals produced by the heart, analyzing the signals for arrhythmia, and providing an appropriate therapy to terminate or reduce the arrhythmia. The pulse generator 701 is coupled to a cardiac lead system having sensing and therapy electrodes 750, 722 electrically coupled to the patient's heart. The cardiac lead system sensing and therapy electrodes 750, 722 may include one or more electrodes positioned in or around the heart as well as one or more electrodes positioned on the housing 790 or header of the pulse generator 701. In one arrangement, the electrodes used for sensing are also used for therapy delivery. In another arrangement, a set of therapy electrodes different from the sensing electrodes is used.

Cardiac signals sensed by sensing electrodes 750 of the cardiac lead system are coupled to an arrhythmia analysis unit 756 configured to identify cardiac arrhythmias. The arrhythmia analysis unit 756 may use information derived from a sleep state processor 752 to provide sleep state informed arrhythmia detection. If cardiac arrhythmia is detected, the therapy unit 742 may provide a number of therapies to treat the detected arrhythmia.

The cardiac therapy may include pacing therapy controlled to treat cardiac rhythms that are too slow. In this situation, the therapy unit 742 controls the delivery of periodic low energy pacing pulses to one or more heart chambers through pacing electrodes of the cardiac lead system 750. The pacing pulses ensure that the periodic contractions of the heart are maintained at a hemodynamically sufficient rate.

The cardiac therapy may also include therapy to terminate tachyarrhythmia, wherein the heart rhythm is too fast. The arrhythmia analysis unit 756 detects and treats episodes of tachyarrhythmia, including tachycardia and/or fibrillation. The arrhythmia analysis unit 756 recognizes cardiac rhythms consistent with various types of tachyarrhythmia. When tachyarrhythmia is identified, the therapy unit 722 may deliver high energy electrical stimulation to the heart through defibrillation electrodes of the cardiac lead system 750 to terminate the arrhythmia.

Implementation of an appropriate cardiac therapy may be augmented using sleep state classification determined by the sleep state processor 752 in accordance with embodiments of the invention. As previously discussed, sleep state classification may be used to determine an optimal arrhythmia therapy. In one example implementation, cardiac therapy may be triggered by signals from the sleep state processor 752 to prevent cardiac arrhythmia during REM or other proarrhythmic sleep periods. In another example, the lower rate limit of a bradycardia pacing regimen may be modified when the sleep state processor 752 indicates that the patient is asleep.

The sleep state processor 752 performs sleep state classification based on one or more sleep-related signals, including at least one REM-modulated signal. In the illustrative embodiment of FIG. 7, a muscle atonia sensor 748, for example, a EMG sensor, provides a REM-modulated signal to the sleep state processor 752. Additionally, a signal responsive to the patient's activity may be used in combination with the REM-modulated signal to augment sleep state classification. In the example implementation illustrated in FIG. 7, the patient activity signal is provided by an accelerometer 746.

The medical device 700 may optionally include components for performing respiratory system analysis 754 and delivering respiration therapy 720. In one embodiment, the patient's respiration patterns may be analyzed with knowledge of the patient's sleep state to determine an appropriate therapy to mitigate detected episodes of disordered breathing or to prevent the occurrence of sleep-disordered breathing.

A transthoracic impedance sensor 744 may be implemented to produce a signal representing the patient's respiration cycles. A respiration analysis unit 754 uses sleep state information provided by the sleep state processor 752 in analyzing the patient's respiration patterns to detect episodes of sleep-disordered breathing. Based on sleep state classification, respiration analysis, and, optionally, cardiac system analysis, respiration therapy may be delivered to the patient to mitigate or prevent respiratory disorders, including sleep apnea, hypopnea, or other forms of disordered breathing. Disordered breathing therapy may include, for example, CPAP therapy, nerve stimulation, or cardiac pacing. According to one embodiment, preventive respiratory therapy may be initiated if the sleep state classification processor indicates the patient is asleep, or upon detection of a particular sleep state.

FIG. 8 is partial view of one embodiment of a medical system that may used to perform sleep state informed therapy, device testing, diagnostic testing or monitoring as previously described. The system illustrated in FIG. 8 represents a cardiac rhythm management (CRM) system 800 capable of sensing physiological signals and providing therapy to treat various cardiac arrhythmias. Embodiments of the CRM system 800 include a medical device 801 that may function as a bradycardia pacemaker, antitachycardia pacemaker, cardioverter, defibrillator, cardiac resynchronizer or any other cardiac rhythm management apparatus capable of sensing the electrical activity of the heart 890 and/or providing therapy to the heart 890.

Components of the CRM system are implantable within the body of a patient at various locations. The medical device 801, e.g., pulse generator may be implanted, for example, in the upper thoracic or pectoral region. Portions of the lead system 802 may be inserted into a right ventricle 818 and right atrium 820 of a patient's heart 890. In other embodiments, the lead system 802 and associated electrodes may be positioned at any internal or external location and in any configuration that provides an effective electrical coupling between the heart 890 and the medical device 801. The lead system 802 may be arranged so that one or more electrodes are disposed in or on the heart 890, or elsewhere, electrically coupling the heart 890 to the medical device 801.

The medical device 801, which may include circuitry for analyzing electrical activity of the heart and delivering therapeutic electrical stimulation to the heart, is disposed within a hermetically sealed housing 810, also referred to as a case or can. In one embodiment, the housing 810 may be covered over its surface with a suitable insulator, e.g., silicone rubber, except for a window that forms an electrode 812 referred to as a case or can electrode. In one embodiment, a header 811 is mounted on the housing 810 for receiving the lead system 802 and electrically coupling the lead system 802 to the circuitry of the medical device 801. In one embodiment, the header 811 includes an electrode referred to as an indifferent electrode 809.

Signals useful in sleep informed operation may be derived from one or more sensors. A muscle atonia sensor may be positioned, for example, in or on the housing 810, on the header 811, or incorporated in the lead system 802 of the medical device 801. In the embodiment illustrated in FIG. 8, a muscle atonia sensor 850 is positioned on the housing 810 of the medical device 801. As previously described, the medical device 801 may be implanted into a pectoral region or other suitable location, allowing access to skeletal muscle by the muscle atonia sensor 850. An accelerometer 860, configured to produce a signal associated with patient activity, may be incorporated within the housing 810 of the pulse generator 801. The muscle atonia sensor 850 and the accelerometer 860 may be used in connection with sleep state classification as previously described. Sleep state classification allows the medical device to deliver sleep state informed cardiac therapy, respiratory therapy, monitoring, testing, or other functions.

The intracardiac lead system 802 may involve various electrodes used in connection with providing electrical stimulation to the heart, sensing electrical activity of the heart, and/or sensing transthoracic impedance or other physiological signals useful in device operation. In the particular embodiment shown in FIG. 8, the intracardiac lead system 802 includes a ventricular lead system 804 and an atrial lead system 805. The ventricular lead system 804 may include an SVC-coil 817, an RV-coil 815, an RV-ring electrode 813, and an RV-tip electrode 812. In various embodiments, combinations of the SVC-coil 817, RV-coil 815 and the can electrode 850 may be used to provide various shock vectors for cardioversion or defibrillation.

According to one illustrative embodiment, the RV-ring 813 and RV-tip 812 electrodes are used for bipolar sensing and pacing of the right ventricle 818. Other combinations of electrodes for sensing, pacing, and shocking are also possible. The atrial lead system 805 includes an A-tip electrode 856 and an A-ring electrode 854 that may be used for bipolar sensing and/or pacing of the right atrium 820.

The medical device 801 may additionally include circuitry for measuring electrical impedance across a portion of the chest or thorax, denoted transthoracic impedance. The transthoracic impedance signal may be used to derive signals related to the patient's respiration, including respiratory minute ventilation or tidal volume. These signals may be used, for example, in connection with adapting a pacing rate to suit the patient's metabolic need. Methods and systems for detecting transthoracic impedance and using the transthoracic impedance to adapt the pacing rate of a cardiac rhythm management system are described in commonly owned U.S. Pat. No. 6,076,015 which is incorporated by reference in its entirety.

The transthoracic impedance signal may also be used in connection to sleep detection and disordered breathing detection. For example, a transthoracic impedance signal may be used in combination with a patient activity signal to implement sleep detection. The transthoracic impedance signal may also be analyzed to detect respiration patterns indicative of disordered breathing episodes.

In one example embodiment, the transthoracic impedance measurement involves delivering an electrical activation signal using one set of electrodes and sensing the response using another set of electrodes. According to one example embodiment, an activation signal is delivered to the heart, for example, using the RV-ring 813 electrode and the RV-tip 812 electrode, or any other electrode configuration suitable for delivering the measurement stimuli. In response to the activation signal, a response signal is sensed, for example, between the RV-tip 812 electrode and the indifferent electrode 809.

Additional configurations of electrodes can be included in the intracardiac lead system 802 to allow for various sensing, pacing, and defibrillation capabilities. In another configuration, the intracardiac lead system may have only a single lead with electrodes positioned in the right atrium or the right ventricle to implement single chamber cardiac sensing and pacing. In yet another configuration, additional electrodes may be positioned adjacent the left atrium and/or the left ventricle to provide left heart chamber sensing and/or pacing. Other lead and electrode arrangements and configurations known in the art are also possible and considered to be within the scope of the present system.

In various configurations, a muscle atonia sensor may be positioned on a housing or header of an implantable cardiac rhythm management device, or may be located on a catheter or lead coupled to the cardiac rhythm management device. A sensor located on a device positioned in the pectoral region provides access to skeletal muscle that may be exploited to detect REM-modulated muscle atonia.

FIGS. 9A-D illustrate various configurations of a muscle atonia sensor mechanically coupled to an implanted medical device 900, such as an implantable pacemaker or implantable cardioverter/defibrillator in accordance with embodiments of the invention. The implantable medical device 900 may include a housing 920 enclosing the medical device circuitry and a header 910 for coupling a lead system 960 to the circuitry of the medical device 900.

Figure 9B:
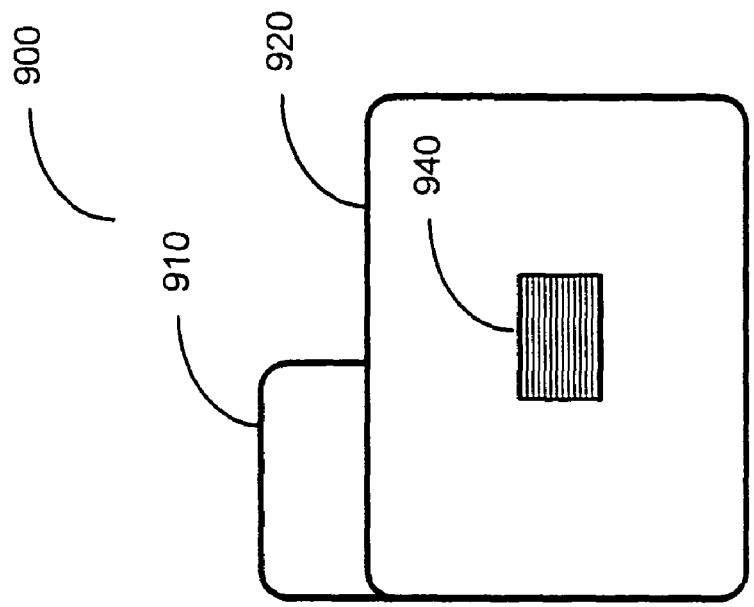
FIGS. 9A-9D are diagrams illustrating various configurations of a muscle atonia sensor coupled to an implanted medical device in accordance with embodiments of the invention.
Figure 9A:
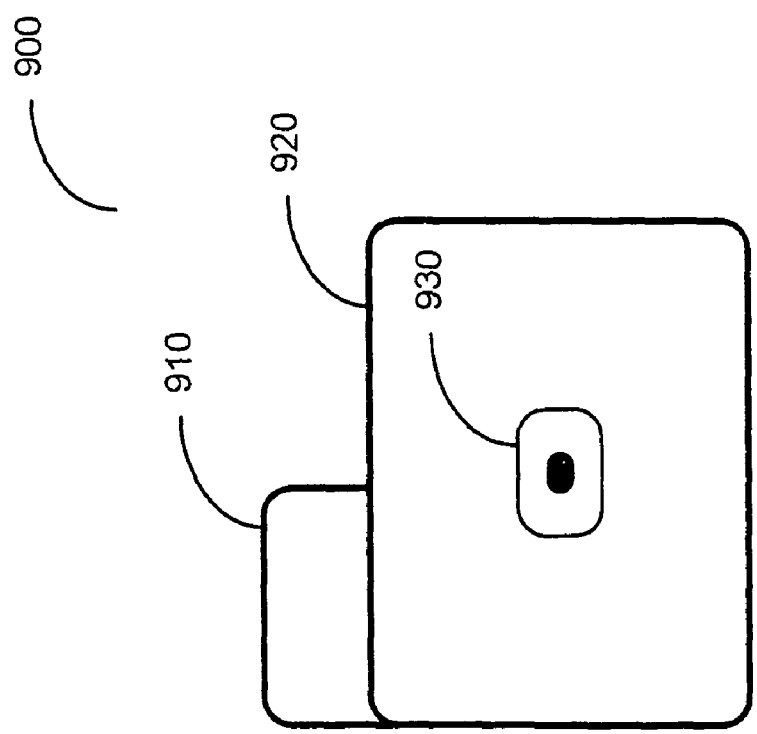
Figure 9D:
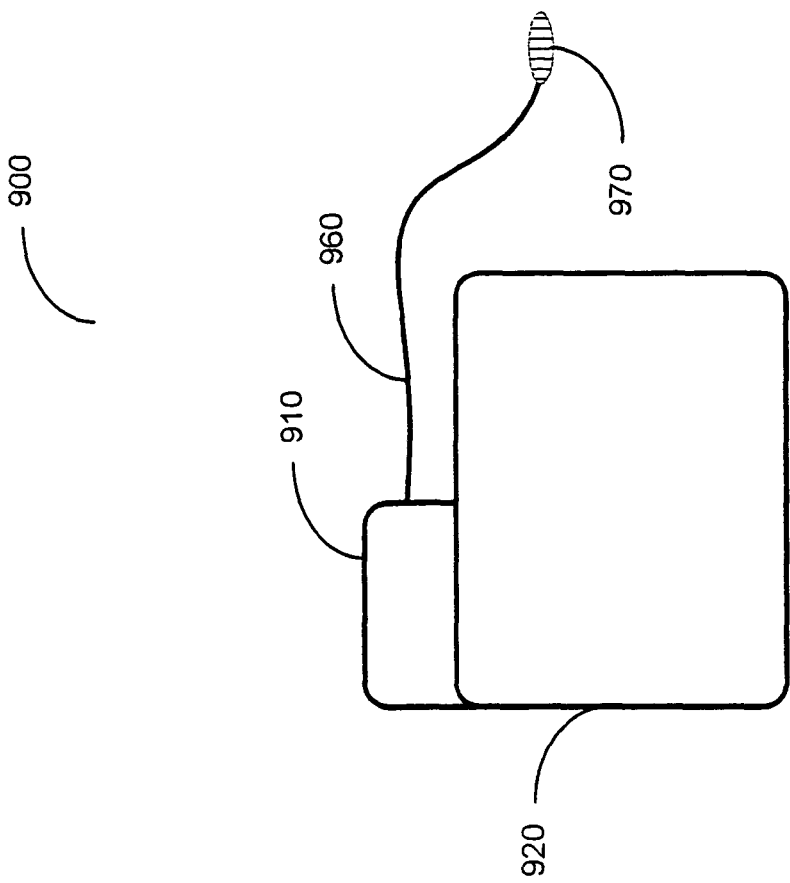
Figure 9C:
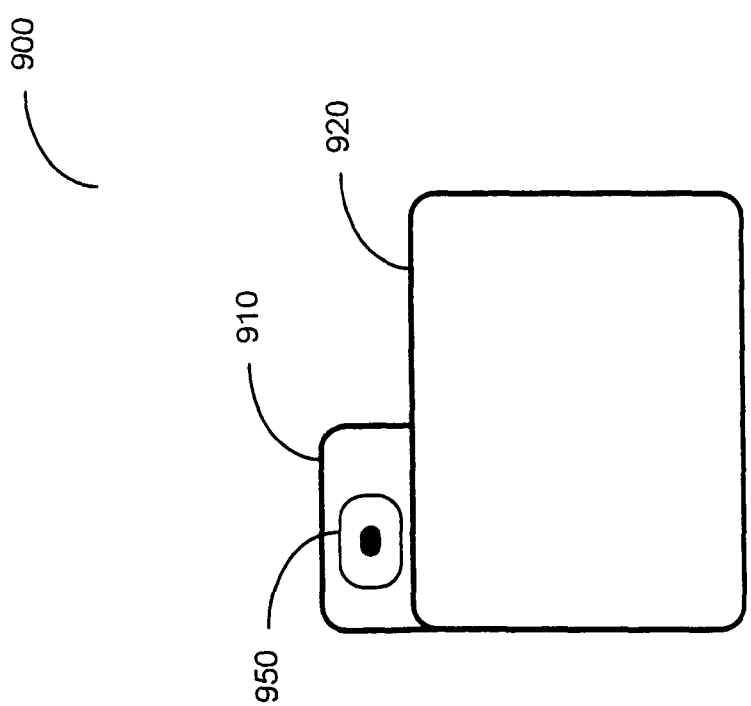

A muscle atonia sensor may be implemented, for example, using an electromyogram (EMG) electrode 930 or force responsive sensor 940 positioned on the housing 920 of the medical device 900 as illustrated in FIGS. 9A and 9B, respectively. FIG. 9C illustrates a muscle atonia sensor 950 positioned on the header 910 of the medical device 900. Alternatively, a muscle atonia sensor 970, e.g., EMG electrode or strain gauge, may be positioned on the lead system 960 or may be coupled to the medical device 900 through a catheter or lead system 960, as illustrated in FIG. 9D.

The following commonly owned U.S. Patents and U.S. Patent Application Publications, some of which have been identified above, are hereby incorporated by reference in their respective entireties: U.S. Pat. No. 7,252,640 (Ni et al.), U.S. Pat. No. 7,189,204 (Ni et al.), U.S. Pat. No. 8,002,553 (Hatlestad et al.), U.S. Pat. No. 7,720,541 (Stahmann et al.), U.S. Pat. No. 7,396,333 (Stahmann et al.), and U.S. Pat. No. 7,680,537 (Stahmann et al.).

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of providing therapy to a patient, comprising:
   sensing a condition associated with a sleep-wake status of a patient;
   detecting the sleep-wake status based on the sensed condition;
   sensing pectoral muscle tone using a sensor disposed on a cardiac rhythm management device implanted in a pectoral region of the patient;
   detecting REM sleep status based on the pectoral muscle tone of the patient;
   classifying one or more sleep states based on the sleep-wake status and the REM sleep status, wherein the classifying, the detecting the sleep-wake status, and the detecting REM sleep status are performed at least in part implantably; and
   providing sleep state informed therapy to the patient using the sleep state classification.

2. The method of claim 1, wherein sensing the muscle tone includes sensing the muscle tone using an electromyogram sensor.

3. The method of claim 1, wherein sensing the muscle tone includes sensing the muscle tone using a sensor on a header of the cardiac rhythm management device.

4. The method of claim 1, wherein the sleep state informed therapy comprises a cardiac therapy.

5. The method of claim 1, wherein the sleep state informed therapy comprises a preventative therapy.

6. The method of claim 1, wherein the condition associated with the sleep-wake status of the patient comprises patient activity.

7. The method of claim 1, wherein sensing the condition associated with the sleep-wake status includes detecting patient activity using an accelerometer.

8. The method of claim 1, wherein sensing the condition associated with the sleep-wake status includes detecting body posture.

9. The method of claim 1, wherein the condition associated with the sleep-wake status includes a patient activity signal, and wherein classifying includes determining sleep onset by comparing the patient activity signal to a sleep threshold.

10. The method of claim 9, wherein classifying also includes determining sleep offset by comparing the patient activity signal to the sleep threshold.

11. The method of claim 1, wherein classifying includes determining REM sleep onset by comparing the pectoral muscle tone to an REM sleep threshold.

12. The method of claim 11, wherein classifying also includes determining REM sleep offset by comparing the pectoral muscle tone to the REM sleep threshold.

13. The method of claim 1, further comprising:
    detecting a cardiac signal;
    wherein the sleep state informed therapy includes bradycardia pacing therapy responsive to the detected cardiac signal and adapted to switch to a lower pacing rate based on the sleep state classification.

14. The method of claim 1, further comprising:
    detecting a cardiac signal;
    wherein the sleep state informed therapy includes preventative arrhythmia therapy responsive to the detected cardiac signal and to the sleep state classification.

15. The method of claim 1, further comprising:
    detecting a cardiac signal;
    analyzing the cardiac signal on a beat-to-beat basis;
    wherein the sleep state informed therapy is responsive to the beat-to-beat cardiac signal analysis.

16. The method of claim 1, further comprising:
    detecting a tidal volume of the patient's respiration; and
    declaring a hypopnea event if the tidal volume falls below a hypopnea threshold.

17. The method of claim 16, further comprising:
declaring an apnea event if the tidal volume falls below an apnea threshold lower than the hypopnea threshold.

18. An implantable cardiac rhythm management device configured to be implanted in a pectoral region of a patient, the device comprising:
a detector system comprising a first and second sensor,
the first sensor disposed on the implantable cardiac rhythm management device, the first sensor configured to sense muscle tone in the pectoral region of the patient and to detect REM sleep status based on the pectoral muscle tone, and
the second sensor configured to detect sleep-wake status of the patient;
a classification system coupled to the detector system and configured to classify sleep state based on the REM sleep status and the sleep-wake status; and
a therapy system coupled to the classification system and configured to provide cardiac therapy to the patient based on the sleep state classification.

19. The device of claim 18, wherein the first sensor is an electromyogram sensor.

20. The device of claim 18, wherein the cardiac rhythm management device comprises:
a housing adapted for implantation in the pectoral region of the patient;
wherein the first sensor is mechanically coupled to the housing.

21. The device of claim 20, wherein the classification system is disposed within the housing.

22. The device of claim 20, wherein the first sensor is positioned on the housing.

23. The device of claim 20, further comprising a header mounted on the housing, and the first sensor is positioned on the header.

24. The device of claim 18,
wherein the cardiac rhythm management device comprises a housing adapted for implantation in the pectoral region of the patient; and
a lead coupled to the housing;
wherein the first sensor is disposed on the lead.

25. The device of claim 18, wherein the second sensor includes an accelerometer.

26. The device of claim 18, wherein the second sensor includes a body posture detector.

27. The device of claim 18, wherein the second sensor is configured to detect a patient activity signal, and wherein the classification system is configured to determine sleep onset by comparing the patient activity signal to a sleep threshold.

28. The device of claim 27, wherein the classification system is also configured to determine sleep offset by comparing the patient activity signal to the sleep threshold.

29. The device of claim 18, wherein the classification system is configured to determine REM sleep onset by comparing the pectoral muscle tone to an REM sleep threshold.

30. The device of claim 29, wherein the classification system is also configured to determine REM sleep offset by comparing the pectoral muscle tone to the REM sleep threshold.

31. The device of claim 18, wherein the detector system further includes a third sensor configured to detect a cardiac signal, and wherein the therapy system is configured to provide bradycardia pacing therapy responsive to the detected cardiac signal and to the sleep state classification.

32. The device of claim 31, wherein the bradycardia pacing therapy is adapted to switch to a lower pacing rate based on the sleep state classification.

33. The device of claim 18, wherein the detector system further includes a third sensor configured to detect a cardiac signal, and wherein the therapy system is configured to provide preventative arrhythmia therapy responsive to the detected cardiac signal and to the sleep state classification.

34. The device of claim 8, wherein the detector system further includes a third sensor configured to detect a cardiac signal, the device further comprising:
an analyzer configured to analyze the cardiac signal on a beat-to-beat basis;
wherein the therapy system is configured to provide therapy based on both the sleep state classification and the beat-to-beat cardiac signal analysis.

35. The device of claim 18, wherein the detector system further includes a third detector configured to detect a tidal volume of the patient's respiration, and wherein the therapy system is configured to declare a hypopnea event if the tidal volume falls below a hypopnea threshold.

36. The device of claim 35, wherein the therapy system is also configured to declare an apnea event if the tidal volume falls below an apnea threshold lower than the hypopnea threshold.

* * * * *

UNITED STATES PATENT AND TRADEMARK OFFICE
CERTIFICATE OF CORRECTION

PATENT NO. : 8,192,376 B2
APPLICATION NO. : 10/643006
DATED : June 5, 2012
INVENTOR(S) : Eric G. Lovett et al.

It is certified that error appears in the above-identified patent and that said Letters Patent is hereby corrected as shown below:

In the Claims

Column 18, line 28, Claim 34: "claim 8," should read --claim 18,--.

Signed and Sealed this
Twenty-eighth Day of August, 2012

David J. Kappos
*Director of the United States Patent and Trademark Office*